(12) United States Patent
Austin

(10) Patent No.: US 8,694,101 B2
(45) Date of Patent: Apr. 8, 2014

(54) COUPLING ELEMENT

(75) Inventor: Eric Austin, Portland, OR (US)

(73) Assignee: Biotronik CRM Patent AG, Baar (CH)

( * ) Notice: Subject to any disclaimer, the term of this patent is extended or adjusted under 35 U.S.C. 154(b) by 1398 days.

(21) Appl. No.: 12/021,139

(22) Filed: Jan. 28, 2008

(65) Prior Publication Data

US 2009/0192573 A1    Jul. 30, 2009

(51) Int. Cl.
*A61N 1/00* (2006.01)

(52) U.S. Cl.
USPC .......................................................... 607/36

(58) Field of Classification Search
USPC .............................................. 607/9, 36, 37, 2
See application file for complete search history.

(56) References Cited

U.S. PATENT DOCUMENTS

| | | | |
|---|---|---|---|
| 4,441,498 A | 4/1984 | Nordling | |
| 6,026,325 A | 2/2000 | Weinberg et al. | |
| 6,626,931 B2 * | 9/2003 | Milla et al. | 607/1 |
| 2002/0095192 A1 * | 7/2002 | Pu et al. | 607/36 |
| 2004/0082977 A1 * | 4/2004 | Engmark et al. | 607/36 |
| 2004/0230250 A1 * | 11/2004 | Neumann et al. | 607/36 |

FOREIGN PATENT DOCUMENTS

WO    WO 2004/039450    5/2004

OTHER PUBLICATIONS

European Search Report dated Jul. 25, 2011 (10 pages).
European Search Report dated Apr. 1, 2011 (6 pages).

* cited by examiner

*Primary Examiner* — Scott Getzow
(74) *Attorney, Agent, or Firm* — ARC IP Law, PC; Joseph J. Mayo

(57) ABSTRACT

An element (1) for mechanical and electrical coupling of a passive and/or active electrical unit (2) to an electrical circuit unit (3). The element (1) comprises at least one electrical contact element (10, 11) for electrical contacting of the passive and/or active electrical unit (2) with electrical circuit unit (3), a first side, which faces toward passive and/or active electrical unit (2), which comprises a second side (13), which faces toward electrical circuit unit (3), and at least one first means (14) for secure mechanical connection to the electrical circuit unit is attached fixed to second side (13). Also discloses an electromedical implant for stimulating human/animal organism and/or sensing human/animal physiological signals. Comprises at least one electrical circuit unit (3), at least one passive and/or active electrical unit (2), and at least one coupling element, to electrically and mechanically couple unit (2) and unit (3) together.

17 Claims, 5 Drawing Sheets

COUPLING ELEMENT

BACKGROUND OF THE INVENTION

1. Field of the Invention

The present invention relates to an element for mechanical and electrical coupling of a passive and/or active electrical unit to an electrical circuit unit. Such elements comprise at least one electrical contact element for the electrical contacting of the passive and/or active electrical unit with the electrical circuit unit and a first side facing toward the passive and/or active electrical unit.

2. Description of the Related Art

The connection of electrical components, such as active and/or passive electrical units, to electrical circuit units plays an especially important role in electrical engineering. In the following, electric or electronic circuits are referred to as electrical circuit units. While the assembly of electrical and/or electromechanical components (switches, lamps, motors . . . ) into a functioning configuration is referred to as an electrical circuit—the function of the circuit being produced by the electrical current which flows through the components in a closed loop (electric circuit), the assembly of electrical and particularly electronic components (such as diodes and transistors) into a (functioning) configuration is referred to as an electronic circuit. An electronic circuit differs from an electrical circuit by the use of electronic components.

Electrical circuit units are located on circuit boards, for example. A circuit board, also referred to as a printed wiring board, printed circuit board, or etched wiring board (printed wiring board=PWB, printed circuit board=PCB, or etched wiring board=EWB), is used for the mechanical fastening and the electrical connection of electronic components. The connection lines are usually produced by etching from a thin layer of conductive material on an insulating base plate. The components are soldered onto these printed conductors. Circuit boards comprise insulating material which may also be flame retardant. Examples of such materials are phenol resin, epoxide resin, glass or glass fibers, Teflon, ceramics, LTCC, HTCC, or polyester.

A secure electrical connection is of great importance in electrical circuit units, to avoid short-circuits, loose contacts, or other malfunctions. For this purpose, fixed electrical connections are important, which are typically made possible by electrically conductive soldering, welding, and/or bonding processes. In such processes, electrically conductive elements of such electrical circuit units are connected to components and/or multiple electrical circuit units are connected to one another to produce entire networks of different circuits. Individual components are also assembled into electrical circuit units by such processes.

Surface-mounting technology (English surface-mounting technology, abbreviated SMT) has developed into the most important method which is most favorable for processing technology in this case. Surface-mounted components (English surface-mounted device, abbreviated SMD or SMD components) are soldered directly on to the circuit board (printed circuit board) using solderable terminal surfaces. This processing is therefore also called assembling, although the assembling also comprises other work steps besides only placing the components on the circuit board. This assembly comprises at least the following steps:

application of soldering paste (a mixture of metal beads (for example: tin beads) and flux) or adhesive to the circuit board
    assembling the components
    soldering the circuit board or curing the adhesive A secure connection of components to electrical circuit units is especially important in medical implants, because implants must operate reliably and may not be maintained or explanted easily. An implant is an artificial material implanted in the body, which is to remain therein permanently or at least for a long period of time. Implants for stimulating the human or animal organism and/or sensing human or animal physiological signals are viewed as electromedical implants in the meaning of the present invention. For example, these are cardiac pacemakers, implantable defibrillators, cardioverters, neurostimulators, or brain pacemakers and artificial hearts. Electromedical implants contain at least one electrical circuit unit, which is capable of analyzing sensed human or animal signals, generating electrical stimulation pulses, storing data from the sensed signals and the stimulation pulses, and/or transmitting the data from the sensed signals and the stimulation pulses out of the body, and at least one passive or active electrical unit.

In such electromedical implants the communication out of the body is—for the above-mentioned reasons of the maintenance or even the programming and/or transmission of physiological states and signals or technical data of the implant—of predominant significance. Such an implant may only be externally programmed by these apparatuses and tailored to the patient and the quality of life may thus be increased. The transmission of data of the implant and threatening or notable states of the body to a treating physician is also important. Only in this way may the physician ensure optimum treatment. For this reason, the above-mentioned electromedical implants have communication means, which allow wireless communication, almost as standard equipment as one of the passive and/or active electrical units. For example, such communication means comprise antennas for near-field or far-field telemetry, which may be coils of any type, above all air-core coils, for example.

Such passive and/or active electrical units may additionally or alternatively comprise one or more of the following components, for example:

capacitors,
    batteries and/or accumulators
    one or more further electrical circuit units, which are capable of analyzing sensed human or animal signals, generating electrical stimulation pulses, storing data from the sensed signals and the stimulation pulses, and/or transmitting the data from the sensed signals and the stimulation pulses out of the body,
    active and/or passive storage units
    filtered or unfiltered feedthroughs Placing passive and/or active electrical units using so-called mounting frames in a housing is known. However, these frames are only used for the defined positioning of the units in this housing and do not offer any further possibilities for electrical and/or mechanical coupling to one another.

Furthermore, providing coils as communication units in electromedical implants, which are welded into laminates—i.e. into plastic films—is known. Two electrical terminal strips are led out of the films, which are electrically contacted manually with an electrical circuit unit via corresponding electrical contacts, in that they are mechanically soldered on manually. This film is connected to the circuit via a gluing method, for example, to thus protect the relatively sensitive terminal strips from being torn off. The disadvantage of this solution is that the production may not be automated, because the laminates may be damaged during SMT processes, for example. The terminal strips are also not or not easily electrically connectable to the circuit via automated processes. In addition, very many work steps having greatly varying parameters are required for the production, because of which the production processes are very time-consuming, work intensive, and thus costly. The electromedical implants cited in this approach are known, for example, from U.S. Pat. No. 4,441,498.

An improvement of the cited solution is presented in WO 2004/039450. A frame element made of a solid plastic material is situated around the communication coil. The terminal strips of the communication coil are electrically contacted and mechanically fastened to contact elements, which are located on the frame element, the contact elements being situated on the outer edge of the frame element in such a way that they also allow an electrical contact to glass-ceramic bushings. The electrical contacting between the communication coil and the electrical circuit unit occurs via a soldering process, in that the contact elements of the frame element are soldered to the circuit. The disadvantage of this solution is that there is only a punctual mechanical fastening between the electrical circuit unit and the frame element having the communication coil, which may easily result in damage and/or tearing off of the contacting in the event of shocks of the electromedical implants. To remove this disadvantage, it has already been described in WO 2004/039450 that in a further work step, planar gluing of the frame element and the communication unit located therein to both the electrical circuit unit and also to a half-shell of the hermetically sealed housing occurs. However, this solution conceals the disadvantage that again an additional work step must be performed, which may not be automated and even requires the application of a further joining technology. The connection to the hermetically sealed housing conceals additional disadvantages, whose solution is not the object of the present invention, however.

BRIEF SUMMARY OF THE INVENTION

Starting from the disadvantages of the prior art, the present invention is based on the object of ensuring the secure, cost-effective electrical and mechanical contacting, which is extensively producible completely automatically and easily, of a passive and/or active electrical unit to an electrical circuit unit, which may be extensively prepared cost-effectively and completely automatically and withstands shocks in the scope of the physically possible.

This object is achieved as claimed herein, in that the element from the preamble comprises a second side, which faces toward the electrical circuit unit, at least one first means for secure mechanical connection to the electrical circuit unit being attached fixed on this second side.

Is important for the observation and understanding of the further embodiment that a mechanical connection has no electrical connection or effect. A mechanical connection in the meaning of the present invention thus has no electrical conduction properties and is to be viewed as an infinite electrical resistor.

This solution has the advantage that in addition to the mechanical coupling, which occurs due to the fixed electrical contacting with the electrical contact element, at least one further mechanical coupling results between the passive and/or active electrical unit and the electrical circuit unit. Secure redundant electrical and mechanical contacting and thus an error-free interaction of the passive and/or active electrical unit and electrical circuit unit are thus made possible. In addition, the extensive security of the contacts from shocks or continuous periodic or rhythmic strains is advantageous.

Furthermore, the present invention offers the advantage that pre-mounting of the passive and/or active electrical unit with the coupling element according to the present invention may be performed, so that simple cost-effective and completely automatic process designs are made possible.

An outer delimitation edge preferably delimits the first and second sides of the element in their extension, which also preferably corresponds to the external contour of an outer delimitation edge of the electrical circuit unit.

This further secures the coupling of passive and/or active electrical unit and electrical circuit unit, because it is thus ensured that in the event of an impact, for example, no edges project or differing forces arise on both units.

In an additional embodiment, an inner delimitation edge delimits the first and second sides of the element in their extension. In a preferred type of the additional embodiment, the inner contour corresponds to an inner delimitation edge of the passive and/or active electrical unit.

In an additional preferred embodiment, the outer and inner delimitation edges run largely parallel and thus form a frame. This results in a savings in material and thus a reduction in weight. Furthermore, such a frame increases the stability of the passive and/or active electrical unit.

In general, the first and second sides of the element may be largely planar surfaces facing away from one another. This improves and simplifies the secure mounting of the passive and/or active electrical unit and the electrical circuit unit and reduces the size of the mounted units.

The at least one contact means of the element for electrical contacting of the passive and/or active electrical unit with the electrical circuit unit may comprise a first and a second end. The first end is used for the electrical contacting with the passive and/or active electrical unit and the second end is used for the electrical contacting with the electrical circuit unit.

The at least one contact means preferably comprises terminal surfaces capable of soldering, bonding, welding, or gluing using an electrically conductive adhesive, which preferably produce a soldered electrical connection between the passive and/or active electrical unit and the electrical circuit unit using a surface-mounting technology (SMT).

The terminal surfaces may also be designed as capable of bonding or welding. It is also possible to set up the terminal surfaces in such a way that a connection using electrically conductive adhesives is made possible.

In a further preferred design, the at least one contact means is located on the second side. The electrical contacts of the passive and/or active electrical unit are brought through at least one opening in the element from the first side to the second side of the element for the electrical contacting.

The cited features simplify the automated mounting of the element according to the present invention with the passive and/or active electrical unit and the electrical circuit unit in as few mounting/process levels as possible. Predefined mounting surfaces are provided, which allow the concrete application of surface-mounting technologies (SMT), which results in simple automation of the mounting.

In a further design, the at least one further means comprises surfaces which are capable of soldering, bonding, welding, or gluing using electrically conductive adhesive. A soldered mechanical connection may preferably be produced between the element according to the present invention and the electrical circuit unit using a surface-mounting technology (SMT) via these surfaces.

This at least one first means is advantageously used for the further secure fastening of the passive and/or active electrical unit to the electrical circuit unit and prevents fastening from only occurring punctually by the electrical contacting at the electrical contacts. Furthermore, the construction allows the simultaneous electrical contacting of the passive and/or active electrical unit with the electrical circuit unit at the electrical contacts and the mechanical connection at the at least one first means for secure mechanical connection by only one process step, for example, an SMT process, which allows extensive automation of the mounting.

In addition, in a further embodiment, a second means may be provided for the secure mechanical fastening of the passive and/or active electrical unit. The second means is electrically and mechanically independent from the first means for the secure mechanical connection to the electrical circuit unit and fastens the passive and/or active electrical unit at the element according to the present invention. The second means preferably comprises dispensed adhesive. Exemplary used is an adhesive with the trademark "Tra-Con Ablebond 400-5" compounded by Tra-Con, Inc. It contributes to further ensuring the electrical contacts between passive and/or active electrical unit and electrical circuit.

Moreover, the element preferably comprises an electrically insulating material, preferably flame retardant materials, especially preferably one of the following materials: phenol resin, epoxide resin, glass or glass fibers, Teflon, ceramics, LTCC, HTTC, or polyester.

The passive and/or active electrical unit is preferably a communication unit, which also allows wireless communication. The communication unit preferably comprises an antenna for near-field or far-field telemetry, especially preferably a coil and more preferably an air-core coil.

Because the use of the element according to the present invention in an electromedical implant is very probable, the present invention is also based on the object of solving the disadvantages of the prior art in regard to electromedical implant, in that more secure operation and secure communication between the extracorporeal area and the electromedical implant are to be ensured.

This object is achieved by as claimed herein, in that, in an electromedical implant, at least one element according to the present invention couples a passive and/or active electrical unit electrically and mechanically to an electrical circuit unit.

For further protection from mechanical strains or damage, the implant also comprises a support frame having struts which enclose the passive and/or active electrical unit on three sides. The support frame is produced from temperature-resistant plastic, preferably from liquid crystal polymer. One example of such polymer and which is exemplarly used is known under trade name Ticona Vectra® T130 LCP.

In a further preferred design, the implant also provides a dispensed adhesive or a adhesive strip for the secure mechanical fastening of the support frame to the passive and/or active electrical unit, the dispensed adhesive or a adhesive strip preferably being electrically insulating, especially preferably comprising an electrically insulating adhesive strip. Exemplary used is an adhesive with the trademark "Tra-Con Ablebond 400-5" compounded by Tra-Con Inc.

Furthermore, the implant comprises a hermetically sealed housing, which encloses the units and means, the housing preferably comprising biocompatible material, especially preferably plastic, medical stainless steel, titanium, or ceramics, and/or alloys made of these materials.

The passive and/or active electrical unit in this implant according to the present invention is preferably a communication unit, which also allows wireless communication. The communication unit preferably comprises an antenna for near-field or far-field telemetry, especially preferably a coil and more preferably an air-core coil.

BRIEF DESCRIPTION OF THE DRAWINGS

In the following, the present invention is described on the basis of an exemplary embodiment having a passive electrical unit in the form of an air-core coil.

DETAILED DESCRIPTION OF THE INVENTION

Figure 1:
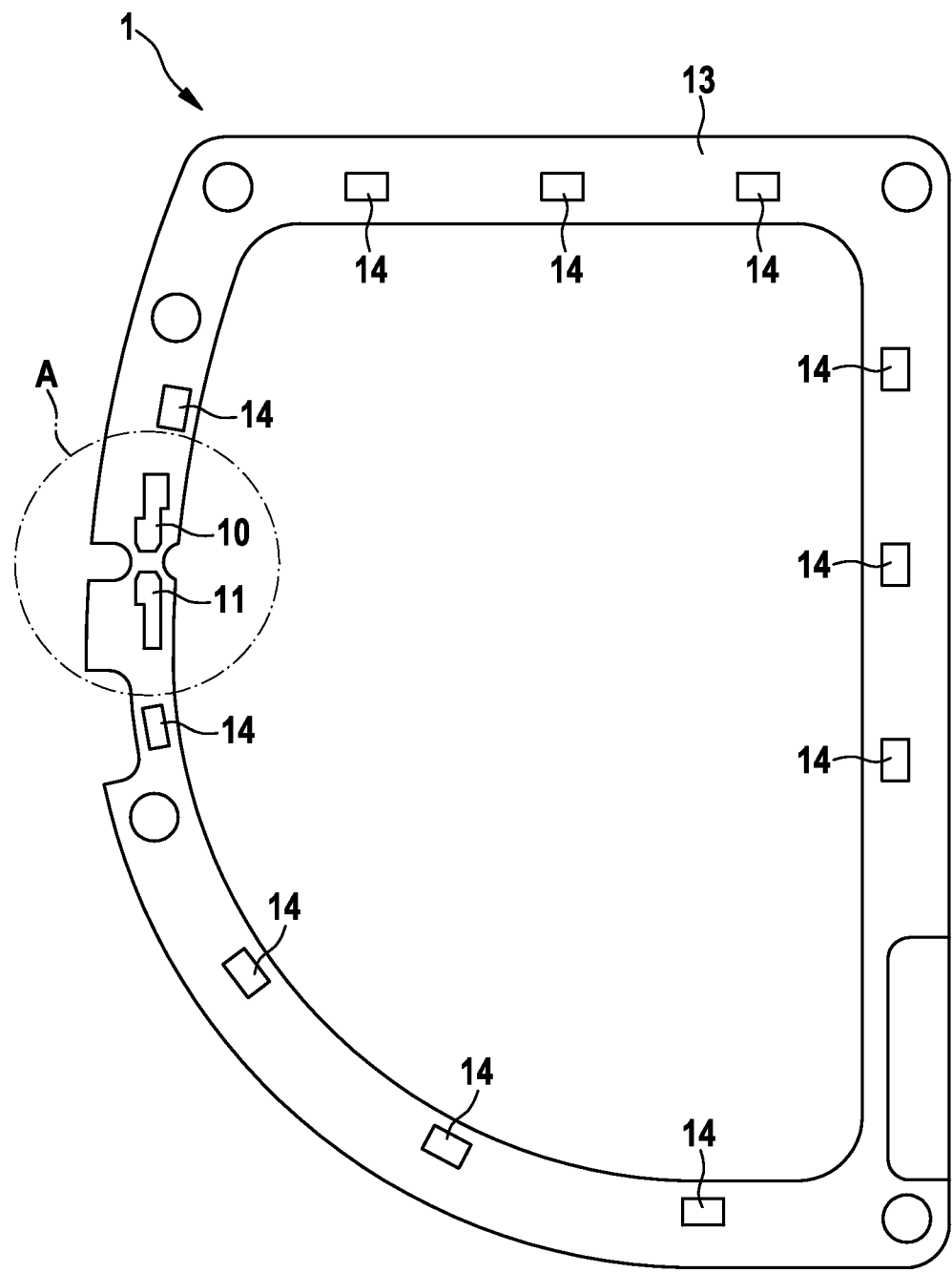
FIG. 1: shows a coupling element according to the present invention in a top view of the second side

The coupling element 1 according to the present invention is shown in FIG. 1 in a view toward the second side 13. The second side is facing toward an electrical circuit unit 3 illustrated in FIG. 4. The coupling element comprises an electrically insulating material, preferably flame retardant materials such as: phenol resin, epoxide resin, glass or glass fibers, Teflon, ceramics, LTCC, HTTC, or polyester.

Two electrical contact elements 10 and 11 are used for the electrical contacting of an air-core coil 2 (also shown in FIG. 4) with the electrical circuit unit 3. The contact elements are only located on the second side 13 and may be attached both connected fixed and also displaceably to the element 1 according to the present invention. If the contact elements 10 and 11 are connected fixed, they have a three-dimensional cuboid shape, five sides being enclosed by the insulating material and a fixed connection thus being produced. However, plates or coatings may also be used.

The exposed surface of the contact elements 10 and 11 is designed as a solderable terminal surface and composed in such a way that a solder contact may be produced using SMT processes.

Furthermore, multiple means 14 for the secure mechanical connection to the electrical circuit unit 3 are attached fixed to the second side 13 of the exemplary embodiment. These means 14 are connected fixed to the element 1. The means have an external surface, which, like the contact elements 10 and 11, are also designed as solderable and composed in such a way that a solder contact may be produced using SMT processes.

Thus, in one work step using SMT processes, both an electrical contact and also a mechanical connection may be produced between an electrical circuit unit 3 and the element according to the present invention.

Figure 2:
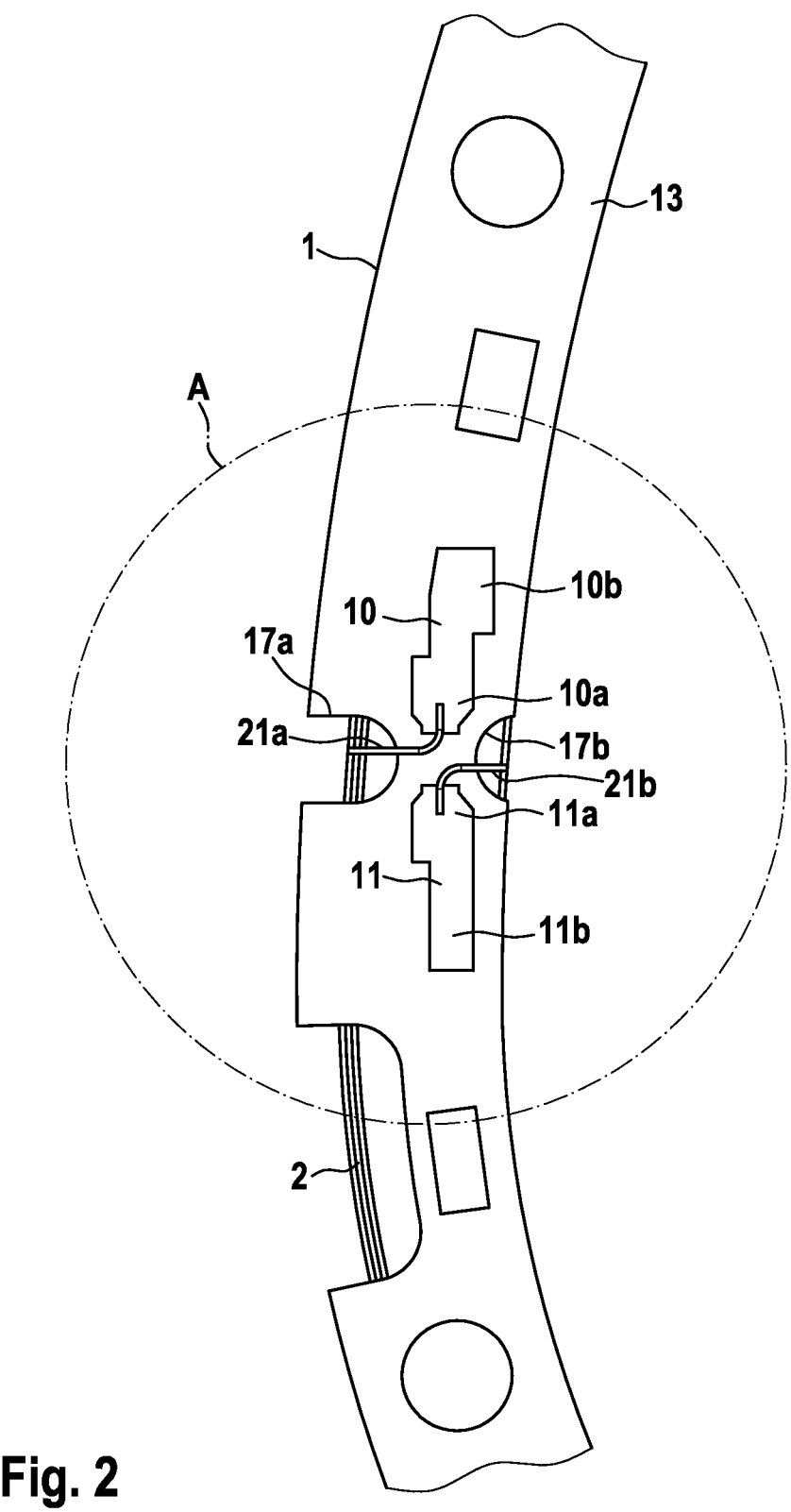
FIG. 2: shows a coupling element according to the present invention in a top view of the second side having pre-mounted air-core coil

FIG. 2 again shows the second side 13 of the element 1 according to the present invention. On a first side (not visible), which forms a surface facing away from the second side, an air-core coil 2 is attached fixed in a pre-mounting step. The second side comprises no surfaces which may be assembled using SMT processes in this exemplary embodiment. Air-core coil 2 is connected fixed in a nonconductive way to the contact element by way of dispensing adhesive at the contacting surfaces between the element 1 and the air-core coil 2. Exemplary used is an adhesive with the trademark "Tra-Con Ablebond 400-5" compounded by Tra-Con Inc. As is recognizable from FIG. 4, the air-core coil 2 also may be connected fixed to the element according to the present invention by using second means for securely mechanical connection of air-core coil 18. In this case this means is a double-sided adhesive film.

The double-sided adhesive film is attached to the element 1 in such a way that the two openings 18a and 18b of the film 18 come to rest congruently to the openings 17a and 17b of the element 1. A continuous opening thus arises, so that the contact strips 21a and 21b of the air-core coil 2, which could be simply the contrary ends of the coil wire unspooled from the main winding of air-core coil 2 for electrical termination, may be led through the openings 17a and 17b to the solderable terminal surfaces of the contact elements 10 and 11, which are attached on the second side 13 facing away from the coil.

The solderable terminal surfaces of the electrical contact elements 10 and 11 have a rectangular shape in this exemplary embodiment, so that they each have a first end 10a and 11a and a second end 10b and 11b. In a further pre-mounting step, at the first end 10a and 11a, the contact strips 21a and 21b of the air-core coil 2 are soldered for example via an SMT process, preferably an automated SMT process, only to the first end 10a and 11a and electrically connected to the solderable terminal surfaces of the electrical contact elements 10 and 11. The air-core coil 2 and the element 1 according to the present invention now form a pre-mounted assembly, which may now be extensively electrically tested.

This SMT process—also referred to as assembly—for pre-mounting comprises at least the following steps:
I. Applying soldering paste (a mixture of metal beads (for example: tin beads) and flux) or adhesive to the circuit board on the first ends 10a and 10b
II. Placing the contact strips 21a and 21b only on the ends 10a and 11a
III. Attaching the contact strips 21a and 21b only to the ends 10a and 11a by soldering, welding (for example spot welding), gluing with electrically conductive adhesive, In the final manufacturing step, in a processing step using a further SMT process, the mechanical coupling and the electrical contacting are performed in that, only at the second ends 10b and 11b of the electrical contact elements 10 and 11 and at the first means 14, the pre-mounted assembly made of element 1 and air-core coil 2 is connected fixed to the electrical circuit unit 3.

Figure 3:
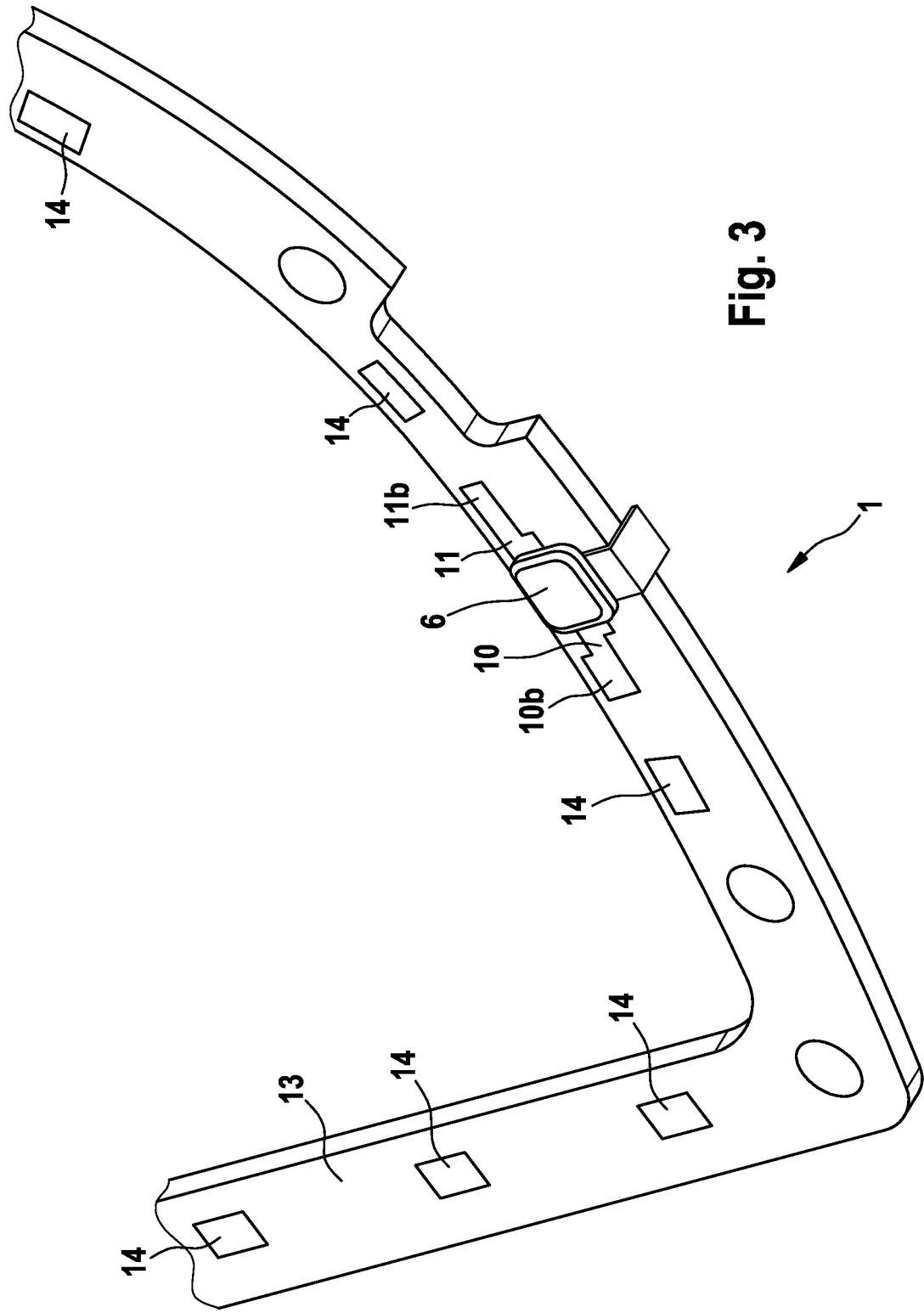
FIG. 3: shows a coupling element according to the present invention in a perspective view having a protective element

This SMT process for final mounting comprises at least the following steps:
I. Applying soldering paste (a mixture of metal beads (for example: tin beads) and flux) or adhesive to the circuit board on the ends 10b, 11b, and the means 14
II. Placing electrical contacts of the electrical circuit unit 3 on the ends 10b and 11b
III. Soldering the electrical contacts of the electrical circuit unit only to the ends 10b and 11b As a further protection of the pre-mounted soldered points, at which the contact strips 21a and 21b are electrically connected to the first ends 10a and 11a of the terminal surfaces of the electrical contact elements 10 and 11, a protective cap is additionally provided. This protective cap is shown in FIG. 3 by the reference numeral 6. The protective cap 6 covers the first ends 10a and 11a of the terminal surfaces of the electrical contact surfaces 10 and 11, the contact strips 21a and 21b, and the openings 17a and 17b. The pre-mounted soldered points may thus not be damaged during the final mounting process. In a further embodiment the protective cap is currently a second type of adhesive, also dispensed only over the first ends 10a and 11a. Exemplarly it could be used an adhesive, known under trade name Hysol 0151.

Figure 4:
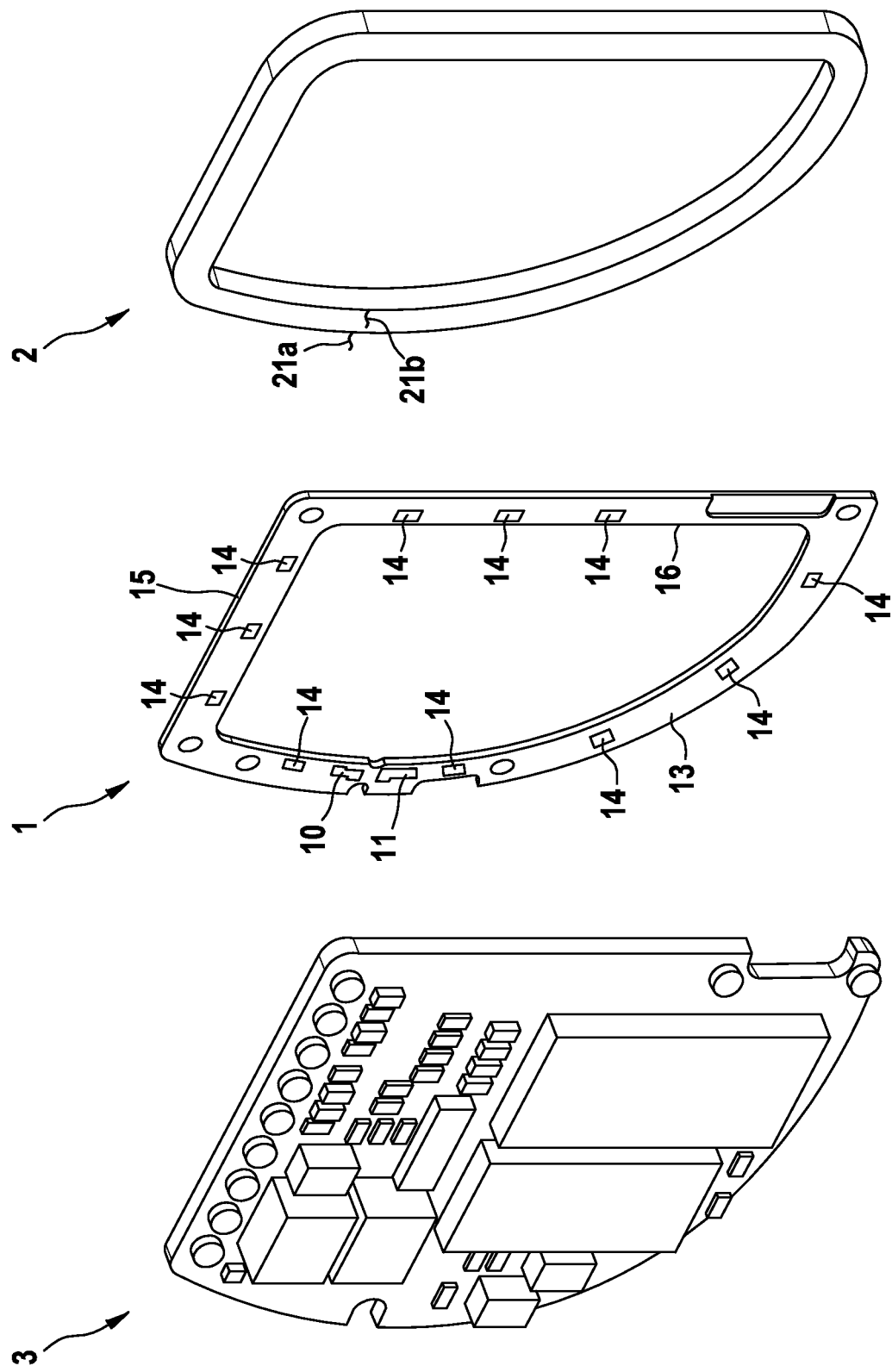
FIG. 4: shows an exploded drawing of a complete construction

FIG. 4 shows an exploded drawing of a complete construction made of the coupling element 1 according to the present invention, which is located between an air-core coil 2 and an electrical circuit unit 3. The element 1 is connected fixed in the assembled state to both the air-core coil 2 and the electrical circuit unit 3. As is obvious from the figure, an outer delimitation edge 15 of the element 1 is visible, which is tailored to the outer contour of the electrical circuit unit 3. The air-core coil or also alternately any other passive and/or active unit 2 is advantageously also the outer contour of the electrical circuit unit 3, because this increases the packing density.

It is also obvious from FIG. 4 that the element 1 has an inner delimitation edge 16, which corresponds to an inner delimitation edge of the air-core coil 2. A frame advantageously arises in this exemplary embodiment, because, as is typical in an air-core coil, the inner contour runs parallel to the outer contour. In this case, the inner contour of the air-core coil 2 and of the element 1 runs parallel to the outer contour of the circuit 3. The opening which is defined by the inner delimitation edge is used for saving material and thus for reducing weight. This is of eminent importance in electro-medical implants above all.

Figure 5:
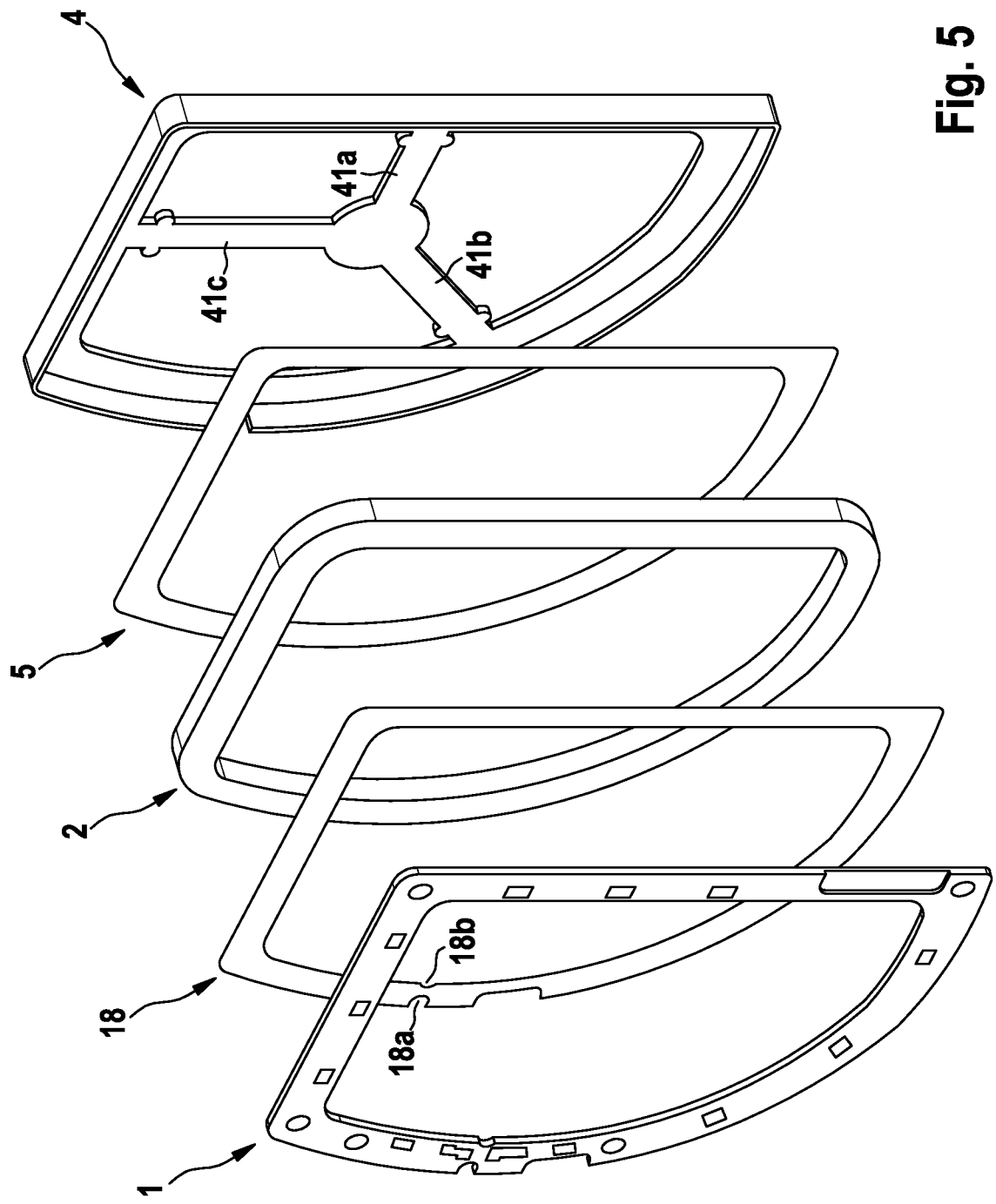
FIG. 5: shows an exploded drawing of the internal construction of an implant according to the present invention having an assembly made of electrical circuit unit, coupling element, and air-core coil

FIG. 5 shows an exemplary internal construction of an implant according to the present invention. Such an implant has a hermetically sealed titanium housing (not shown here), in which, inter alia, the illustrated components are integrated. A coupling element 1 is securely mechanically and electrically connected via electrical contact elements 10 and 11, which may be processed by SMT, and via at least one means 14 for mechanical coupling to an electrical circuit unit 3 (not shown here). An air-core coil 2 is securely mechanically connected on the side of the coupling element 1 opposite to the electrical circuit unit using dispensing adhesive or a second means 18. The electrical contact between the air-core coil 2 and the electrical coupling elements 10 and 11 is produced via the contact strips 21a and 21b. The "contact strips" could also be simply the contrary ends of coil wire, unspooled from the main winding, for electrical termination.

The coil must be suitably protected due to the continuous rhythmic and arrhythmic shocks which an electromedical implant is subjected to in a body. For this reason, a support frame 4 is connected to the air-core coil 2 by way of dispensing adhesive at the contacting surfaces between the element 1 and the air-core coil 2. Exemplary used is an adhesive with the trademark "Tra-Con Ablebond 400-5" compounded by Tra-Con Inc. It is also possible to connect fixed the support frame to the air-core coil 2 using a third mechanical means 5. The third means 5 is produced from the same material from which the second means 18 is produced. As an further important function, support frame 4 protects the coil from damage during inner device assembly during manual or automatic assembly steps.

The support frame 4 encloses the coil in such a way that only the surface of the air-core coil 2 which is attached to the first side of the coupling element 1 is not protected. The air-core coil 2 is thus protected on all external sides in the assembled state.

To increase the stability, the support frame 4 has struts 41a, 41b, and 41c. In addition to stability, also a purpose of the three-strut structure of struts 41a, 41b and 41c is to present a round, flat surface for the complete assembled coil assembly to be picked up with a movable vacuum tip, and placed on the electrical circuit 3 by automated assembly equipment during the SMT process.

LIST OF REFERENCE NUMBERS

1 . . . Coupling element
2 . . . electrical unit, for example air-core coil
3 . . . electrical circuit unit
4 . . . support frame
5 . . . third mechanical means for securely mechanical connection of support frame 6 ... protective cap
10 ... electrical contact element
10a ... first end of electrical contact element
10b ... second end of electrical contact element
11 ... electrical contact element
11a ... first end of electrical contact element
11b ... second end of electrical contact element
13 ... second side of coupling element
14 ... means for secure mechanical connection
15 ... outer delimitation edge of coupling element
16 ... inner delimitation edge of coupling element
17a ... opening in coupling element
17b ... opening in coupling element
18 ... second means for securely mechanical connection of air-core coil
18a ... opening in second means for securely mechanical connection of air-core coil
18b ... opening in second means for securely mechanical connection of air-core coil
21a ... contact strip of air-core coil
21b ... contact strip of air-core coil
41a ... strut of support frame
41b ... strut of support frame
41c ... strut of support frame

What is claimed is:

1. A coupling element (1) configured to mechanically and electrically couple a passive and/or active electrical unit (2) to an electrical circuit unit (3), comprising:
    at least one electrical contact element (10, 11) configured for electrical contact of the passive and/or active electrical unit (2) with the electrical circuit unit (3);
    at least one mechanical coupling (14) configured to mechanically couple said the electrical circuit unit (3);
    a first side, which faces toward the passive and/or active electrical unit (2);
    a second side (13), which faces toward the electrical circuit unit (3), wherein said at least one mechanical coupling (14) is fixedly attached to the second side (13);
    wherein the at least one electrical contact element (10, 11) comprises terminal surfaces that form a soldered electrical connection to provide said electrical contact between the passive and/or active electrical unit (2) and the electrical circuit unit (3), through use of a surface-mounting technology; and,
    wherein the at least one mechanical coupling (14) comprises surfaces that form a soldered mechanical connection between the coupling element (1) and the electrical circuit unit (3), through use of said surface-mounting technology, but which does not provide said electrical contact between the passive and/or active electrical unit (2) and the electrical circuit unit (3).

2. The coupling element according to claim 1, further comprising an outer delimitation edge (15) that delimits the first side and second side (13) in their extension and corresponds to an outer contour of a first delimitation edge of the electrical circuit unit (3).

3. The coupling element according to claim 1, further comprising an inner delimitation edge (16) that delimits the first side and second side (13) in their extension and corresponds to an inner contour of an inner delimitation edge of the passive and/or active electrical unit (2).

4. The coupling element according to claim 1, further comprising outer and inner delimitation edges (15, 16) that run extensively parallel and thus form a frame.

5. The coupling element according to claim 1 wherein the first side and second side (13) are largely planar surfaces facing away from one another.

6. The coupling element according to claim 1, wherein the at least one electrical contact element (10, 11) comprises a first end (10a, 11a) configured for electrical contact with the passive and/or active electrical unit (2) and a second end (10b, 11b) configured for electrical contact with the electrical circuit unit (3).

7. The coupling element according to claim 1, wherein the at least one electrical contact element (10, 11) is located on the second side (13) and wherein electrical contacts (21a, 21b) of the passive and/or active electrical unit (2) are brought through at least one opening (17a, 17b) from the first side to the second side (13).

8. The coupling element according to claim 1, wherein the passive and/or active electrical unit (2) is a communication unit, which allows wireless communication and comprises an antenna for near-field or far-field telemetry, wherein said antenna comprises a coil or an air-core coil.

9. The coupling element according to claim 1, further comprising a second means (18) configured to securely mechanically fasten the passive and/or active electrical unit (2), the second means being electrically and mechanically independent from the at least one mechanical coupling (14) wherein said second means fastens the passive and/or active electrical unit (2) to the element (1).

10. The coupling element according to claim 9, wherein the second means comprises dispensed adhesives.

11. The coupling element according to claim 1, wherein the coupling element comprises electrically insulating material, flame retardant material, including at least one of the following materials: phenol resin, epoxide resin, glass or glass fibers, Teflon, ceramics, LTCC, HTTC, or polyester.

12. An electromedical implant for stimulating the human or animal organism and/or for sensing human or animal physiological signals, comprising:
    at least one electrical circuit unit (3), which analyzes sensed signals selected from sensed human or animal signals and/or generates electrical stimulation pulses and/or stores data from the sensed signals and the electrical stimulation pulses and/or transmits the data from the sensed signals and the electrical stimulation pulses out of a body of a human or animal;
    at least one passive and/or active electrical unit (2);
    a coupling element (1) configured to mechanically and electrically couple the at least one passive and/or active electrical unit (2) to the at least one electrical circuit unit (3), comprising
        at least one electrical contact element (10, 11) configured to mechanically and electrically couple the at least one active and/or passive electrical unit (2) and the electrical circuit unit (3) to one another;
        at least one mechanical coupling (14) configured to mechanically couple said electrical circuit unit (3) with said coupling element (1);
        a first side, which faces toward the passive and/or active electrical unit (2);
        a second side (13), which faces toward the electrical circuit unit (3), wherein said at least one mechanical coupling (14) is fixedly attached to the second side (13);
        wherein the at least one electrical contact element (10, 11) comprises terminal surfaces that form a soldered electrical connection between the passive and/or active electrical unit (2) and the electrical circuit unit (3), through use of a surface-mounting technology; and,
        wherein the at least one mechanical coupling (14) comprises surfaces that form a soldered mechanical connection between the coupling element (1) and the electrical circuit unit (3), through use of said surface-mounting technology, but which does not provide said electrical contact between the passive and/or active electrical unit (2) and the electrical circuit unit (3).

13. The implant according to claim 12, further comprising a support frame (4) having struts (41*a*, 41*b*, 41*c*), which encloses the passive and/or electrical unit (2) on three sides.

14. The implant according to claim 13, wherein the support frame (4) is produced from heat-resistant plastic, or from liquid crystal polymer.

15. The implant according to claim 13 wherein a dispensed adhesive or an adhesive strip (5) is provided to securely mechanically fasten the support frame (4) to the passive and/or active electrical unit (2), the dispensed adhesive or adhesive strip being electrically insulating.

16. The implant according to claim 12 housed in a hermetically sealed housing that encloses said implant, the housing comprising biocompatible material, including at least one of the materials: plastic, medical stainless steel, titanium, or ceramics, and/or alloys made of these materials.

17. The implant according to one of claim 12 wherein the passive and/or active electrical unit comprises a communication unit for allowing wireless communication, which comprises an antenna for near-field or far-field telemetry, wherein said antenna comprises a coil or an air-core coil.

* * * * *